United States Patent
Rather et al.

(10) Patent No.: US 11,944,609 B1
(45) Date of Patent: Apr. 2, 2024

(54) ANTIFUNGAL IONIC LIQUID AND AMPHOTERICIN B COMBINATION

(71) Applicant: KING ABDULAZIZ UNIVERISTY, Jeddah (SA)

(72) Inventors: Sami-ullah Rather, Jeddah (SA); Mohmmad Younus Wani, Jeddah (SA); Hisham S. Bamufleh, Jeddah (SA); Hesham Alhumade, Jeddah (SA); Usman Saeed, Jeddah (SA); Aqeel Ahmad Taimoor, Jeddah (SA); Walid M. Alalayah, Jeddah (SA); Irfan Ahmad Rather, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

(21) Appl. No.: 18/336,107

(22) Filed: Jun. 16, 2023

(51) Int. Cl.
*A61K 31/437* (2006.01)
*A61K 31/7048* (2006.01)
*A61P 31/10* (2006.01)
*C07D 471/04* (2006.01)

(52) U.S. Cl.
CPC ........ *A61K 31/437* (2013.01); *A61K 31/7048* (2013.01); *A61P 31/10* (2018.01); *C07D 471/04* (2013.01)

(58) Field of Classification Search
None
See application file for complete search history.

(56) References Cited

U.S. PATENT DOCUMENTS

2021/0353565 A1* 11/2021 Mitragotri .............. A61K 31/14

FOREIGN PATENT DOCUMENTS

SU        813921 A   * 12/1986

OTHER PUBLICATIONS

Miyashita, M., Akamatsu, M., Ueno, H., NAKAGAwA, Y., NiSHiMURA, K., HAYAsHI, Y., . . . & Ueno, T. (1999). Structure-activity relationships of RGD mimetics as fibrinogen-receptor antagonists. Bioscience, biotechnology, and biochemistry, 63(10), 1684-1690. (Year: 1999).*
Petronilho, A., Mueller-Bunz, H., & Albrecht, M. (2015). Iridium, ruthenium, and palladium complexes containing a mesoionic fused imidazolylidene ligand. Journal of Organometallic Chemistry, 775, 117-123. (Year: 2015).*
Esson, M. M., & Mecozzi, S. (2020). Preparation, characterization, and formulation optimization of ionic-liquid-in-water nanoemulsions toward systemic delivery of amphotericin B. Molecular Pharmaceutics, 17(6), 2221-2226. (Year: 2020).*
Suchodolski, J., Feder-Kubis, J., & Krasowska, A. (2021). Antiadhesive Properties of Imidazolium Ionic Liquids Based on (−)-Menthol Against *Candida* spp. International Journal of Molecular Sciences, 22(14), 7543. (Year: 2021).*

* cited by examiner

*Primary Examiner* — Dale R Miller
(74) *Attorney, Agent, or Firm* — WCF IP (57) ABSTRACT

Provided herein are ionic liquids that can be used as antifungal agents alone or in combination with Amphotericin B. Also disclosed are methods of synthesis of the ionic liquids and inhibiting fungal growth and methods of treating fungal infections using the disclosed compounds. The disclosure provides antifungal agents that potentiate the antifungal activity of Amphotericin B, a commonly used antifungal drug that could be used alone or in combination. This combination will help control and combat the infections caused by drug resistant *Candida. auris* in immunocompromised patients.

7 Claims, 5 Drawing Sheets

ANTIFUNGAL IONIC LIQUID AND AMPHOTERICIN B COMBINATION

FIELD OF THE INVENTION

The disclosure provides antifungal agents that potentiate the antifungal activity of Amphotericin B, a commonly used antifungal drug that could be used alone or in combination. This combination will help control and combat the infections caused by drug resistant *Candida. auris* in immunocompromised patients.

BACKGROUND

The World Health Organization (WHO) has designated more than 200 antibiotic molecules and formulations for use and application under the AWaRe classification to limit the emergence of antibiotic resistance while maintaining the efficacy of these molecules in clinical settings. Resistance to practically all kinds of antimicrobial medications is significantly increasing. Fungal infections affect more than a billion people, resulting in approximately 11.5 million life-threatening infections and more than 1.5 million deaths annually. The high rate of mortality associated with invasive fungal infections, which often exceeds 50%, despite the availability of antifungal drugs, is particularly concerning and worrying.

Amphotericin B is a potent antifungal medication that treats fungal infections, including serious and invasive fungal infections. It belongs to the class of polyene antifungal drugs and is considered a first-line treatment option for severe fungal infections, although associated with severe toxicity and bioavailability issues. Liposomal formulations of Amphotericin B have been used to reduce the incidence and severity of side effects. In recent years ionic liquids have drawn the attention of researchers in the medical sciences because of their vast structural diversity and modification of structures for achieving desirable antimicrobial activities. Despite the efficacy of Amphotericin B against invasive fungal infections, the side effects and toxicity associated with it sometimes require discontinuation of the therapy. Nephrotoxicity is a significant concern, especially with prolonged or high-dose therapy. Poor water solubility and membrane permeability also limit its use.

Some articles describing the use of ionic liquids alone or in combination with other antifungal drugs to treat fungal infections: Molecules 27 (2022) 6650; Molecules 28 (2023) 3432; RSC Advances 11(2021) 14441; Microbiological Research 197 (2017) 56-64; ACS Biomater. Sci. Eng. 6 (2020) 3832-3842; The Journal of Infectious Diseases 133 (1976) 206-209; International Journal of Pharmaceutics 589 (2020) 119842; New England Journal of Medicine 376 (2017) 2329-2340; iScience 24 (2021) 101853; Front. Microbiol. 11(2020) 730; Green Chem. 11 (2009) 492-497; Lett. Appl. Microbiol. 60 (2014) 66-71; Lett. Appl. Microbiol. 61 (2015) 504-510; RSC Advances 12 (2022) 1922-1931.

The World Health Organization (WHO) notes that fungal pathogens are a significant threat to public health as they are becoming "increasingly common and resistant to treatment with only four classes of antifungal medicines currently available" and few candidates in the clinical pipeline. Up to 95% of all invasive *Candida* infections in the United States are caused by non-*albicans Candida* species. Although *C. albicans* is still the leading cause of candidemia, increasing proportions of cases in recent years have been attributed to non-*albicans* species resistant to antifungal drugs. *C. auris* is an emerging multidrug-resistant fungal pathogen associated with nosocomial infections and presents a serious global health threat.

Centers for Disease Control (CDC) is concerned about this pathogen because it is often multi-drug resistant, is difficult to identify using standard laboratory methods, and has caused outbreaks in healthcare settings. About 90% of *C. auris* isolates in the United States have been resistant to fluconazole, about 30% have been resistant to amphotericin B, and less than 5% have been resistant to echinocandins. Therefore, urgent and serious steps needed to be taken to prevent any outbreaks that could prove devastating.

Unlike most bacterial diseases, fungal diseases are difficult to treat. Additionally, systemic candidiasis is linked with a high mortality rate in immunocompromised individuals. In the past few years, the escalating use of drugs for the treatment of *Candida* infections ranging from superficial to invasive has resulted in the emergence of drug-resistant strains of *Candida*. Therefore, developing a potential anti-*Candida* agent with lesser toxicities has become a high priority in the field. Moreover, individuals suffering from conditions such as HIV/AIDS, organ transplantation, and chemotherapy are expected to rise over the next ten years, and these patients are susceptible to *Candida* infections with serious side effects. Thus, the requirement for a novel anti-*Candida* agent with targeted action is increasing.

The emergence of multi-drug-resistant *Candida* strains has been widely reported in the past few years, and it is well demonstrated that these resistant phenotypes can emerge over the period of infection and even in response to the treatment process, which poses an additional threat to sick patients. Furthermore, these infections put a significant economic burden on the individual.

Despite increasing numbers of health-compromised people prone to life-threatening fungal infection, only four classes of antifungal drugs are approved by the USFDA for treating infections caused by *Candida* species. These drugs include polyenes, azoles, echinocandins, and flucytosine. Although current medications could prevent infections, the problem arises when the microbes develop resistance to different defense mechanisms.

The polyene class of antifungals is associated with dose-related toxicity, mainly nephrotoxicity; however, the discovery of lipid formulations has lowered the risk factors. Further, of more importance, increasing drug resistance is an unavoidable problem. The reduction of fluconazole susceptibility in some *candida* strains, especially *C. auris*, is becoming a challenge for HIV patients, although second-generation antifungals (triazole agents and echinocandins) have addressed some issues. However, treatment failures and the advent of resistance against echinocandin antifungal agents have been reported, and therefore, the mortality rates for candidemia remain high. This situation thus emphasizes the pressing need for more effective and less toxic antifungal agents against *C. auris* infection.

Among the various approaches that are being used to fight multidrug-resistant pathogens, combination therapy is sought out to be a practical approach that could improve the activity profile of an otherwise ineffective drug or provide a more effective way to treat drug resistant pathogens. Combination antifungal therapy involves the simultaneous use of two or more antifungal drugs to treat fungal infections. It is often employed in specific situations where monotherapy may be inadequate or when dealing with difficult-to-treat or resistant fungal infections. For example, Amphotericin B and flucytosine are commonly used to treat severe cryptococcal meningitis. Amphotericin B is effective against *Cryp-* tococcus neoformans, while flucytosine enhances its activity and helps prevent the development of resistance. Similarly, Azoles and echinocandins are utilized to manage invasive candidiasis, particularly in critically ill patients. Azole and terbinafine combination is also used in some cases of difficult-to-treat dermatophyte infections like onychomycosis. Therefore, a combination of a known antifungal drug with a potentiator is a useful strategy to fight multidrug resistance and resolve toxicity issues associated with some drugs like amphotericin B.

SUMMARY

In light of the disadvantages of the prior art, the following summary is provided to facilitate an understanding of some of the innovative features unique to the present invention and is not intended to be a complete description. A full appreciation of the various aspects of the invention can be gained by taking the entire specifications, claims, drawings, and abstract as a whole.

Provided herein are antifungal agents that potentiate the antifungal activity of Amphotericin B, a commonly used antifungal drug that could be used alone or in combination to treat *C. auris* infections. In particular, these molecules control and comb Embodiments of the disclosure provide new molecules (Ionic liquids), having the following formula:

wherein
X is Br, Cl, I, or any counter ion; and
R is an alkyl chain of varying lengths (C4-C12).

The ionic liquids comprise an organic cation (Imidazopyridinium ion) with an alkyl chain or varying length and an inorganic anion (bromide). These Ionic liquids are liquids at room temperature.

In some embodiments, the length of the alkyl chain can be 4C, 6C, 8C, 10C, 12C, or more. In some embodiments, the inorganic cation can be bromide, chloride, iodide, or any other counter ion.

Further embodiments provide a pharmaceutical composition comprising an ionic liquid, amphotericin B, and a pharmaceutically acceptable carrier. "Pharmaceutically" or "pharmaceutically acceptable" refers to molecular entities and compositions that do not produce an adverse, allergic, or other untoward reaction when administered to a mammal, especially a human, as appropriate. A pharmaceutically acceptable carrier or excipient refers to a non-toxic solid, semi-solid, or liquid filler, diluent, encapsulating material, or formulation auxiliary of any type.

Suitable pharmaceutically acceptable carriers include but are not limited to water, salt solutions, alcohols, gum arabic, vegetable oils, benzyl alcohols, polyethylene glycols, gelate, carbohydrates such as lactose, amylose or starch, magnesium stearate talc, silicic acid, viscous paraffin, perfume oil, fatty acid monoglycerides and diglycerides, pentaerythritol fatty acid esters, hydroxymethylcellulose, polyvinylpyrrolidone, etc. The pharmaceutical preparations can be sterilized and, if desired, mixed with auxiliary agents, e.g., lubricants, preservatives, stabilizers, wetting agents, emulsifiers, salts for influencing osmotic pressure buffers, coloring, flavoring and/or aromatic substances, and the like. Other suitable excipients include an inert diluent such as lactose; granulating and disintegrating agents such as cornstarch; binding agents such as starch; and lubricating agents such as magnesium stearate.

In another embodiment of the present disclosure, the excipient in the composition is selected from the group consisting of additive, solvent, oil, emulsifier, surfactant, stabilizer, cooling agent, preservative, antioxidant, gelling agent, moisturizing agent, emollient, penetration enhancer, colorant, fragrance, pH modifiers, conditioning agent, pearlizing agents, skin barrier repair agents, and combinations thereof.

The composition may contain additional ingredients to provide the composition in a form suitable for administration. The final amount of compound in the formulations may vary. However, in general, the amount in the formulations will be from about 1% to about 99%.

In some embodiments, the composition is an oily solution or suspension. In some embodiments, the formulation is in a solid dosage form, such as a form selected from the group consisting of a tablet, dragee, capsule, caplet, and gelcap.

In embodiments, the composition is employed for the purpose of topical and/or local administration in the form of oils, creams, lotions, serums, gels, ointments, foams, sprays, aerosols, coating on implants, silicon tubes, catheters, sutures and the like.

In some embodiments, the composition comprises one or more additional antifungal agents. Suitable antifungal agents include but are not limited to, allylamines, benzylamines, azoles, polyenes, echinocandins, N-hydroxy pyridone, N-hydroxy pyrithione, tavaborole, flucytosine, griseofulvin, hinokitol and combinations thereof. In some embodiments, the N-hydroxy pyridone is piroctone olamine, ciclopirox olamine or a combination thereof; the N-hydroxy pyrithione is zinc pyrithione or any respective bivalent metal coordinating complexes or combinations thereof; allylamines are selected from the group consisting of terbinafine, amorolfine, naftifine and combinations thereof; the benzylamine is butenafine; the azoles are imidazoles, triazoles or thiazoles selected from the group consisting of ketoconazole, climbazole, miconazole nitrate, fluconazole, econazole, saperconazole, oxiconazole, clotrimazole, bifonazole, butoconazole, fenticonazole, isoconazole, omoconazole, sertaconazole, sulconazole, tioconazole, luliconazole, chlormidazole, croconazole, eberconazole, omoconazole, isoconazole, neticonazole, albaconazole, efinaconazole, fosfluconazole, epoxiconazole, fluconazole, isavuconazole, itraconazole, posaconazole, propiconazole, ravuconazole, terconazole, voriconazole, hexaconazole, abafungin and combinations thereof; the polyenes are selected from the group consisting of natamycin, nystatin and combinations thereof; and the echinocandins are selected from the group consisting of caspofungin, anidulafungin, micafungin and combinations thereof.

Embodiments of the present disclosure further provide methods of inhibiting the growth of a fungus comprising contacting the fungus with an adequate amount of an ionic liquid-Amphotericin B combination, as described herein. In some embodiments, the method is for treating a fungal infection in a subject in need thereof or managing fungal growth, comprising administering the ionic liquid alone or in combination with Amphotericin B or pharmaceutical composition described herein to the subject.

In an embodiment of the present disclosure, the method of treating or managing comprises inhibiting the fungal growth, reducing the fungal growth, eliminating the fungus, curing drug resistant fungal infections, treatment of fungal infections in clinical non-responders and patients with barrier defects, or any combination thereof.

In another embodiment of the present disclosure, the treatment described herein includes medical treatment, cosmetic treatment, or a combination thereof.

The methods and uses described herein may further include treating a subject in need thereof, comprising the steps of administering the complex or composition in an oral delivery vehicle, food product, nutritional supplement, dietary supplement, or functional food comprising the formulation to the subject. In some embodiments, the administration is oral, topical, parenteral, enteral, transdermal, intradermal, intraocular, intravitreal, sublingual, or intravaginal and may preferably comprise an effective amount of the complex or composition.

In some embodiments, the composition is administered concomitantly or sequentially with one or more additional antifungal agents as described herein.

A patient or subject to be treated by any of the compositions or methods of the present disclosure can mean either a human or a non-human animal including, but not limited to, dogs, horses, cats, rabbits, gerbils, hamsters, rodents, birds, aquatic mammals, cattle, pigs, camelids, and other zoological animals.

In some embodiments, the fungal infection or fungal growth is caused by fungi selected from the group consisting of *Candida* species, *Malassezia* species, *Trichophyton* species, *Microsporum* species, *Epidermophyton* species, *Aspergillus* species, *Cryptococcus* species and combinations thereof.

In another embodiment of the present disclosure, the fungal infection or fungal growth is caused by *Candida* spp. selected from the group consisting of *C. auris, C. albicans, C. glabrata, C. guilliermondii, C. krusei, C. lusitaniae, C. parapsilosis, C. tropicalis, C. colliculosa, C. dubliniensis, C. famata, C. haemulonii, C. inconspicua, C. intermedia, C. kefyr, C. lipolytica, C. metapsilosis, C. norvegensis, C. orthopsilosis, C. pelliculosa, C. pulcherrima, C. rugosa, C. utilis, C. viswanathii,* and *C. zeylanoides; Malassezia* spp. selected from the group consisting of *M. furfur, M. pachydermatis, M. globosa, M. restricta, M. sloofiae, M. sympodialis, M. nana, M. yamatoensis, M. dermatis, M. obtusa, M. japonica, M. caprae, M. cuniculi, M. equine,* and *M. arunalokei; Trichophyton* spp. selected from the group consisting of *T. rubrum, T. mentagrophyte, T. interdigitale, T. tonsurans, T. schoenleinii, T. violaceum, T. abissinicum, T. balcaneum, T. circonvolutum, T. concentricum, T. eboreum, T. errinacei, T. fischeri, T. fluviomuniense, T. glabrum, T. gourvilii, T. kanei, T. kuryangei, T. megninii, T. pedis, T. proliferans, T. raubitschekii, T. redellii, T. rodhainii, T. simii, T. soudanense, T. thuringiense, T. verrucosum, T. violaceum* and *Trichophyton yaoundei; Microsporum* spp. selected from the group consisting of *M. audouinii, M. canis, M. amazonicum, M. boullardii, M. cookie, M, distortum, M. duboisii, M equinum, M. ferrugineum, M. fulvum, M. gallinae, M. gypseum, M. langeronii, M. nanum, M. persicolor, M. praecox, M. ripariae* and *M. rivalieri; Epidermaphyton* spp such as *E. floccosum*; and other non-dermatophytes including but not limited to *Aspergillus* spp. selected from the group consisting of *A. fumigates, A. flavus, A. nidulans, A. terreus, A. lentulus, A. niger, A. alliaceus, A. arvii, A. brevipes, A. calidoustus, A. conjunctus, A. deflectus, A. duricaulis, A. emericella, A. fscherian, A. fumigatiaffinis, A. fumisvnnematus, A. granulosus, A. novofumigatus, A. panamensis, A. quadrilineatus, A. udagawae, A. unilateralis* and *A. ustus*; and *Cryptococcus* spp. selected from the group consisting of *C. neoformans, C. gattii, C. albidus, C. bacillisporus, C. decagatti, C. deuterogatti, C. laurentii, C. tetragatti* and *C. uniguttulatus*; or any combination of fungi thereof.

In some embodiments, the fungus is resistant or susceptible to an anti-fungal agent, as described herein. Without wishing to be bound by a theory, the compositions described herein are particularly useful for the treatment of fungal infections resistant to one or more conventional drugs used for the treatment of fungal infections. For example, the compositions of the invention are particularly useful for the treatment of fungal infections which are resistant to azoles (e.g., fluconazole), allylamines, benzylamines, or Amphotericin B.

As used herein, the terms "manage," "managing," "management," "treat," "treating," or "treatment" of fungus growth or fungus infection refers to both medical or non-medical indications. In one aspect, these terms cover one or more aspects including but not limiting to preventing or reducing the growth of fungi, inhibiting further growth of fungi, eliminating the grown fungi at the infected area/site, providing symptomatic relief to a subject in need thereof, successfully eliminating the infection, curing the fungal infection, preventing recurrence of fungal infection, curing drug resistant fungal infections, and treatment of fungal infections in clinical non-responders and patients with barrier defects.

In some embodiments, the composition is administered to the subject in a therapeutically effective amount. By a "therapeutically effective amount" is meant a sufficient amount of active agent to treat the disease or disorder at a reasonable benefit/risk ratio applicable to any medical treatment. It will be understood that the total daily usage of the compositions of the present invention will be decided by the attending physician within the scope of sound medical judgment. The specific therapeutically effective dose level for any particular subject will depend upon a variety of factors, including the disorder being treated and the severity of the disorder, activity of the specific compound employed; the specific composition used, the age, body weight, general health, sex and diet of the subject; the time of administration, route of administration, and rate of excretion of the specific compound employed; the duration of the treatment; drugs used in combination or coincidental with the specific active agent employed; and like factors well known in the medical arts. For example, it is well within the skill of the art to start doses of the compound at levels or frequencies lower than those required to achieve the desired therapeutic effect and to gradually increase the dosage or frequency until the desired result is achieved. However, the daily dosage of the active agent may be varied over a wide range from 0.01 to 1,000 mg per adult per day. In particular, the compositions contain 0.01, 0.05, 0.1, 0.5, 1.0, 2.5, 5.0, 10.0, 15.0, 25.0, 50.0, 100, 250, 500, and 1,000 mg of the active ingredient for the symptomatic adjustment of the dosage to the subject to be treated. An adequate amount of the drug is ordinarily supplied at a dosage level from 0.0002 mg/kg to about 20 mg/kg of body weight per day, especially from about 0.001 mg/kg to 7 mg/kg of body weight per day. In some embodiments, the composition is administered daily or 2, 3, 4, 5, 6, 7, or more times weekly.

Embodiments of the disclosure also include methods of preparing the ionic liquids as described herein. Such methods may utilize conventional organic chemistry techniques, e.g., as described in the Example herein. For example, embodiments provide a method for synthesis of ionic liquids (ICP4-ICP12) with the chemical composition and formula 1-Butylimidazo[1,2-a]pyridinium bromide (IPC4), 1-Hexylimidazo[1,2-a] pyridinium bromide (IPC6), 1-Octylimidazo[1,2-a] pyridinium bromide (IPC8), 1-Decylimidazo[1, 2-a] pyridinium bromide (IPC10), and 1-Dodecylimidazo[1, 2-a] pyridinium bromide (IPC12), under conditions suitable for forming the ionic liquids.

It is to be understood that this invention is not limited to any particular embodiment described herein and may vary. It is also to be understood that the terminology used herein is for the purpose of describing particular embodiments only and is not intended to be limiting since the scope of the present invention will be limited only by the appended claims.

Where a range of values is provided, it is understood that each intervening value between the upper and lower limit of that range (to a tenth of the unit of the lower limit) is included in the range and encompassed within the invention unless the context or description clearly dictates otherwise. In addition, smaller ranges between any two values in the range are encompassed unless the context or description indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each publication or patent were specifically and individually indicated to be incorporated by reference and are incorporated herein by reference to disclose and describe the methods and/or materials in connection with which the publications are cited. The citation of any publication is for its disclosure before the filing date. It should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a," "an," and "the" include plural referents unless the context clearly dictates otherwise. It is further noted that the claims may be drafted to exclude any optional element. As such, this statement is intended to serve as support for the recitation in the claims of such exclusive terminology as "solely," "only," and the like in connection with the recitation of claim elements or use of a "negative" limitations, such as "wherein [a particular feature or element] is absent," or "except for [a particular feature or element]," or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLE

Methods

Figure 1:
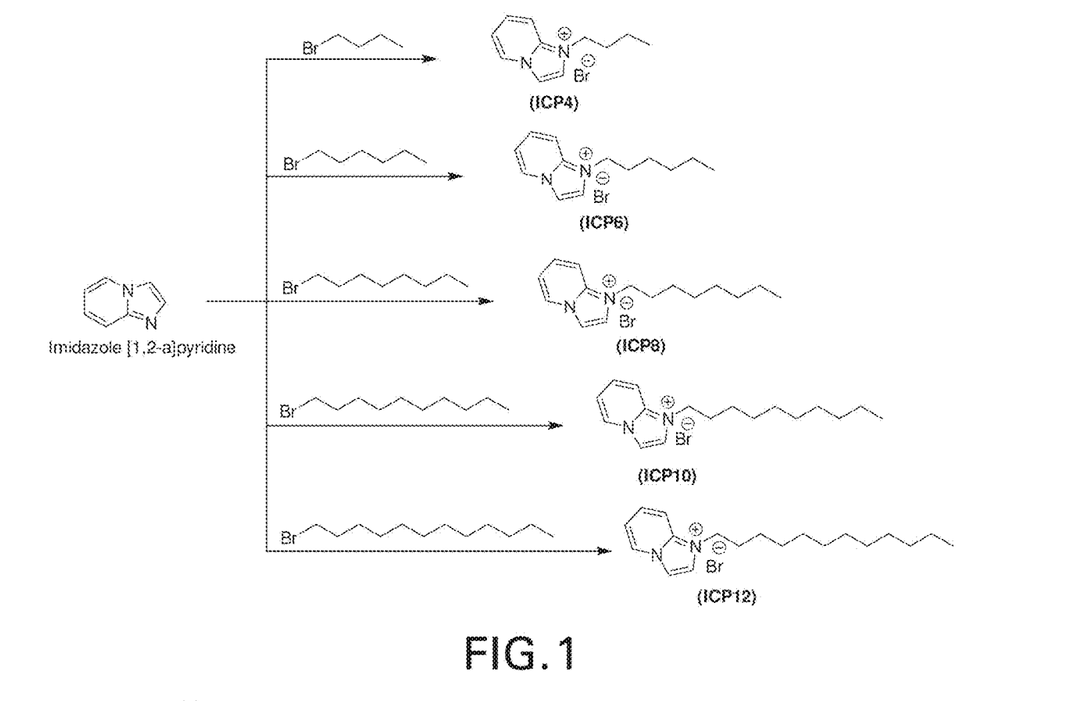

As shown in FIG. 1, the ionic liquids (ICP4-ICP12) were synthesized by treating the respective 1-bromo alkanes (0.166 mol) dropwise to imidazole [1,2-a]pyridine (0.126 mol) in a three necked round bottom flask in an ice bath with constant stirring for 30 min. Then the products were kept undisturbed by wrapping in the aluminum foil for 24 hours. After that, the products were dissolved in acetonitrile and dried in a vacuum to remove the solvent. All the products were washed with ether to remove impurities and characterized by different physical and spectroscopic techniques.

1-Butylimidazo[1,2-a] pyridinium bromide (IPC4)

$^1$HNMR (DMSO-d6) δ(ppm): 9.10-7.60 (m, 6H, Ar), 4.48 (t, 2H, $CH_2$), 1.92-1.87 (p, 2H, $CH_2$), 1.39-1.28 (m, 2H, $CH_2$), 0.98-0.94 (t, 3H, $CH_3$); $^{13}$CNMR (DMSO-d6) δ(ppm): 137.01, 131.80, 127.96, 123.69, 115.40, 113.49, 109.50, 45.04, 29.43, 20.38, 12.06; FTIR $v_{max}$ cm$^{-1}$: 3090 (C—H str, Imd ring), 2850-2970 (C—H str, alkyl chain), 1530-1650 (Imd ring str), 1450-1460 (C=C), 1350-1400 (C—N, Imd ring); UV-Vis (λ max): 320, 450 nm.

1-Hexylimidazo[1,2-a] pyridinium bromide (IPC6)

$^1$HNMR (DMSO-d6) δ(ppm): 9.04-7.52 (m, 6H, Ar), 4.50 (t, 2H, $CH_2$), 2.07-1.77 (p, 2H, $CH_2$), 1.33-1.20 (m, 6H, $CH_2$), 0.89-0.78 (t, 3H, $CH_3$); $^{13}$CNMR (DMSO-d6) δ(ppm): 136.97, 131.76, 127.91, 124.03, 115.36, 113.65, 109.47, 45.02, 29.33, 23.57, 20.11, 17.25, 12.01; FTIR $v_{max}$ cm$^{-1}$: 3090 (C—H str, Imd ring), 2850-2970 (C—H str, alkyl chain), 1530-1650 (Imd ring str), 1450-1460 (C=C), 1350-1400 (C—N, Imd ring); UV-Vis (λ max): 320, 450 nm.

1-Octylimidazo[1,2-a] pyridinium bromide (IPC8)

$^1$HNMR (DMSO-d6) δ(ppm): 9.06-7.53 (m, 6H, Ar), 4.51 (t, 2H, $CH_2$), 1.85-1.80 (p, 2H, $CH_2$), 1.29-1.16 (m, 10H, $CH_2$ chain), 0.81-0.77 (t, 3H, $CH_2$); $^{13}$CNMR (DMSO-d6) δ(ppm): 136.96, 131.75, 127.90, 123.67, 115.36, 113.57, 109.50, 45.02, 29.34, 27.32, 26.71, 26.68, 23.57, 20.22, 12.09; FTIR $v_{max}$ cm$^{-1}$: 3090 (C—H str, Imd ring), 2850-2970 (C—H str, alkyl chain), 1532-1645 (Imd ring str), 1451 (C=C), 1372 (C—N, Imd ring); UV-Vis (λ max): 320, 450 nm.

1-Decylimidazo[1,2-a] pyridinium bromide (IPC10)

$^1$HNMR (DMSO-d6) δ(ppm): 8.98-7.52 (m, 6H, Ar), 4.47 (t, 2H, $CH_2$), 1.86-1.79 (p, 2H, $CH_2$), 1.27-1.20 (m, 14H, $CH_2$ chain), 0.84-0.81 (t, 3H, $CH_3$); $^{13}$CNMR (DMSO-d6) δ(ppm): 139.23, 133.98, 130.17, 127.90, 125.88, 115.71, 113.60, 47.23, 32.97, 29.50, 29.43, 29.30, 29.13, 28.94, 26.17, 22.52, 14.39; FTIR $v_{max}$ cm$^{-1}$: 3090 (C—H str, Imd ring), 2850-2970 (C—H str, alkyl chain), 1530-1650 (Imd ring str), 1450-1460 (C=C), 1350-1400 (C—N, Imd ring); UV-Vis (λ max): 320, 450 nm.

1-Dodecylimidazo[1,2-a] pyridinium bromide (IPC12)

$^1$HNMR (DMSO-d6) δ(ppm): 9.02-7.53 (m, 6H, Ar), 4.47 (t, 2H, $CH_2$), 1.86-1.79 (p, 2H, $CH_2$), 1.26-1.14 (m, 18H, $CH_2$ chain), 0.80-0.77 (t, 3H, $CH_3$); $^{13}$CNMR (DMSO-d6) δ(ppm): 137.06, 131.82, 128.00, 123.72, 115.46, 113.60, 109.52, 45.08, 29.56, 27.36, 27.27, 27.14, 26.97, 26.79, 24.01, 20.36, 12.21; FTIR $v_{max}$ cm$^{-1}$: 3090 (C—H str, Imd ring), 2850-2970 (C—H str, alkyl chain), 1530-1650 (Imd ring str), 1450-1460 (C=C), 1350-1400 (C—N, Imd ring); UV-Vis (λ max): 320, 450 nm.

In this work, the antifungal activity of the ionic liquids (IPC4-IPC12) against *C. auris* was investigated in terms of minimum inhibitory concentration (MIC) and minimum fungicidal concentration (MFC). A stock solution of 20 mg/mL was prepared in 1% Dimethyl sulfoxide (DMSO; Sigma-Aldrich, USA). Fourteen different concentrations of test ILs were prepared by performing serial dilution in a flat bottom 96-well microtiter plate, followed by the addition of *C. auris* cells (0.5×10³-2.5×10³ cells/mL; 100 µL) which gave us the final test concentrations of ILs (5000-0.61 µg/mL). Amphotericin B was used as a positive control, 1% DMSO as a negative control, and drug-free control was used in each set of experiments. The optical density was determined at a wavelength of 600 nm using SpectraMax iD3 multi-mode microplate reader, and the concentration resulting in 100% inhibition was picked up as the MIC value. Post-MIC evaluation, MFC was estimated by administrating 10 µL of samples from the wells displaying MIC and beyond on a Sabouraud Dextrose Agar (SDA) plate. The plates were incubated at 35±2° C. for 24 h, and the concentration resulting in no visible colonies was documented as MFC value for respective ionic liquids.

The in vitro time-kill assay was conducted to understand the correlation between the concentration of the most promising derivative (IPC8) and various time points during the growth of *C. auris*, this data provides detailed information compared to antifungal susceptibility testing alone. The assay for determining the time-kill kinetics values of IPC8 against *C. auris* was carried out at various concentrations (½, 1, 2, and 4 times the MIC) against *C. auris*. The *C. auris* cell suspension with a starting inoculum of around $1 \times 10^5$ to $5 \times 10^5$ CFU/mL was incubated with/without IPC8 at $35°$ C.$\pm 2°$ C. and 150 rpm. Aliquots (100 µL) were taken out at predetermined time points (0, 2, 4, 6, 8, 12, and 24 h), and for determining CFU counts, the aliquots were serially diluted in sterile water and plate (20 µL) on SDA growth medium. The plates were incubated at $35°$ C.$\pm 2°$ C. for 24 to 48 h, and the number of colonies was counted using a colony counter. The experiment was performed in duplicate, and the result is articulated in log 10 viable CFU/mL.

The type of interaction between ionic liquids and amphotericin B against *C. auris* was evaluated by the checkerboard microdilution method. The concentrations of ionic liquids used ranged from 5000-0.61 µg/mL, and amphotericin B was 64-0.06 µg/mL. Subsequently, equal volumes (50 µL) of ionic liquids and amphotericin B were dispensed into predetermined wells, which were further supplemented with *C. auris* cells ($0.5 \times 10^3$-$2.5 \times 10^3$ cells/mL; 100 µL) followed by incubation at $35 \pm 2°$ C. for 24 h. Also, each experiment included DMSO (1%) was added as negative control along with growth and sterility controls. The combination concentration of the ionic liquids and amphotericin B that resulted in around 100% growth inhibition was considered the MIC value. The interaction between the test compounds and amphotericin B was deduced according to the calculated coefficient of the sum of fractional inhibitory concentrations (ΣFIC). This experiment was followed by nine varied ratio combinations (10:90, 20:80, 30:70, 40:60, 50:50, 60:40, 70:30, 80:20, and 90:10), and isobolograms were made for only those combinations which showed synergistic interaction in 1:1 combination ratio.

$$FICI = FICa + FICb = \frac{MICa \text{ in combination}}{MICa \text{ alone}} + \frac{MICb \text{ in combination}}{MICb \text{ alone}}$$

MICa=MIC of the ionic liquids; MICb=MIC of amphotericin B. The FICI values were interpreted as ΣFIC≤0.5, synergy; ΣFIC>0.5-≤1, additivity; ΣFIC>1-<2, no interaction; ΣFIC≥2, antagonism.

The cytotoxicity of IPC8 on horse red blood cells (H-RBC) was checked by conducting a cytotoxicity assay. Briefly, the RBC was separated from the horse blood and was thoroughly washed with NaCl (150 mM) solution. Thereafter, RBC suspension (2%) was prepared in sterile PBS, followed by the addition (180 µL) to a microcentrifuge tube containing IPC12 (20 µL) in graded concentrations (1.22 µg/mL, 4.88 µg/mL, 19.53 µg/mL and 39.06 µg/mL), the microcentrifuge tubes were kept aside for 45 min at $37°$ C. followed by centrifugation at 1300×g for 5 min. The supernatant (100 µL) was collected in a separate tube and mixed with 900 µL of sterile PBS. Aliquots (200 µL) were taken from each dilution and transferred to a 96-well flat bottom microtiter plate, and optical density was measured at 540 nm (SpectraMax iD3 multi-mode microplate reader, Molecular Devices). The negative control contained RBC suspension in PBS, and the positive control had RBC treated with 0.1% Triton X-100. To calculate the percentage of hemolysis below formula was used.

$$\text{Percentage hemolysis} = \frac{[\text{Absorbance of } RBC \text{ treated with test compound} - \text{Absorbance of blank}]}{[\text{Absorbance of } RBC \text{ treated with 0.1\% tritonix} - 100 - \text{Absorbance of blank}]} \times 100$$

Statistical analysis for all the experiments was performed in triplicate and final outcomes were analysed by GraphPad Prism® using a two-way ANOVA test. Statistical significance was calculated in terms of p value (*$p<0.001$, $p<0.01$, and *$p<0.1$).

Results

Characterization of the Compounds

As shown in FIG. 1, the ionic liquids (ICP4-ICP12) were synthesized by treating the respective 1-bromo alkanes (0.166 mol) dropwise to imidazole [1,2-a]pyridine (0.126 mol) in a three necked round bottom flask in an ice bath with constant stirring for 30 min. The physicochemical properties that include viscosity and density of the ionic liquids ICP4-ICP12 are given in Table 1. The viscosity measurements of the ionic liquids were performed in an automated RHEOSENSE MicroVisc Portable Viscometer, United States, at atmospheric pressure and 298K ($\pm 0.15$). Each measurement was taken in triplicate, and in doing so, it has been observed that viscosity values were reproducible with an accuracy of $\pm 0.01$ mPa. The density measurement of all ILs performed by automated Density Meter DMA 501, Anton Paar, at 298 K and atmospheric pressure. The uncertainties in the density measurements, considering the sample handling and purity, are determined to be with an accuracy of 0.0001 g/cm3.

TABLE 1

Viscosity and density measurements of the ionic liquids ICP4-ICP12.

| Name | Viscosity (mPa) | Density (g/cm$^3$) |
|---|---|---|
| IPC4 | 4.14 | 1.0310 |
| IPC6 | 14.7 | 1.0102 |
| IPC8 | 25.21 | 1.0094 |
| IPC10 | 27.20 | 1.0081 |
| IPC12 | 28.60 | 1.0049 |

Figure 2:
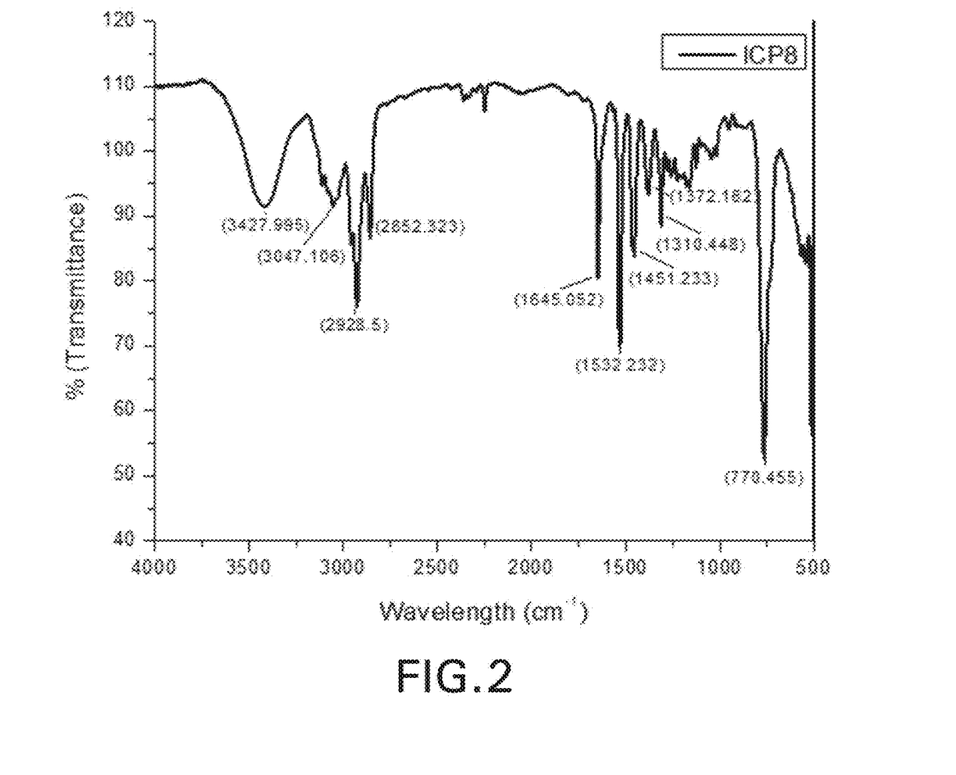

The infrared spectra showed characteristic bands that established the structures of the ionic liquids. Aromatic C—H stretching bands appeared between 3047-3100 cm$^{-1}$, while aliphatic stretching C—H bands appeared around 2852 and 2950 cm$^{-1}$. At the same time, C—C vibrations in the imidazole ring appeared between 1532 and 1645 cm$^{-1}$. Stretching bands around 1451 cm$^{-1}$ are related to aromatic C=C. The stretching bands of CN (vibration modes) in the imidazole ring were found in the 1372-1400 cm-1 range. A representative FTIR spectrum of ICP8 is given in FIG. 2.

FIG. 2

Figure 3:
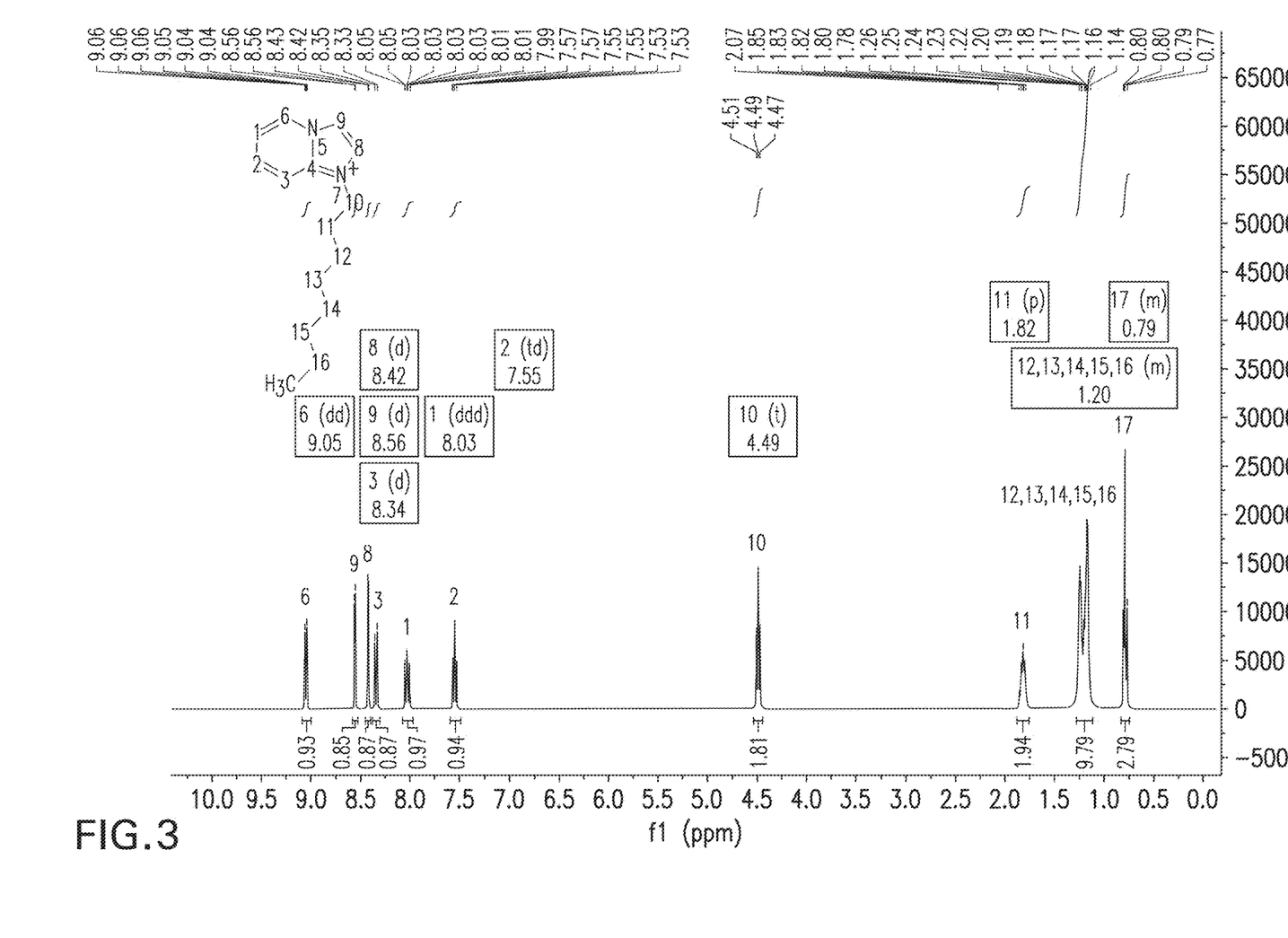
Figure 4:
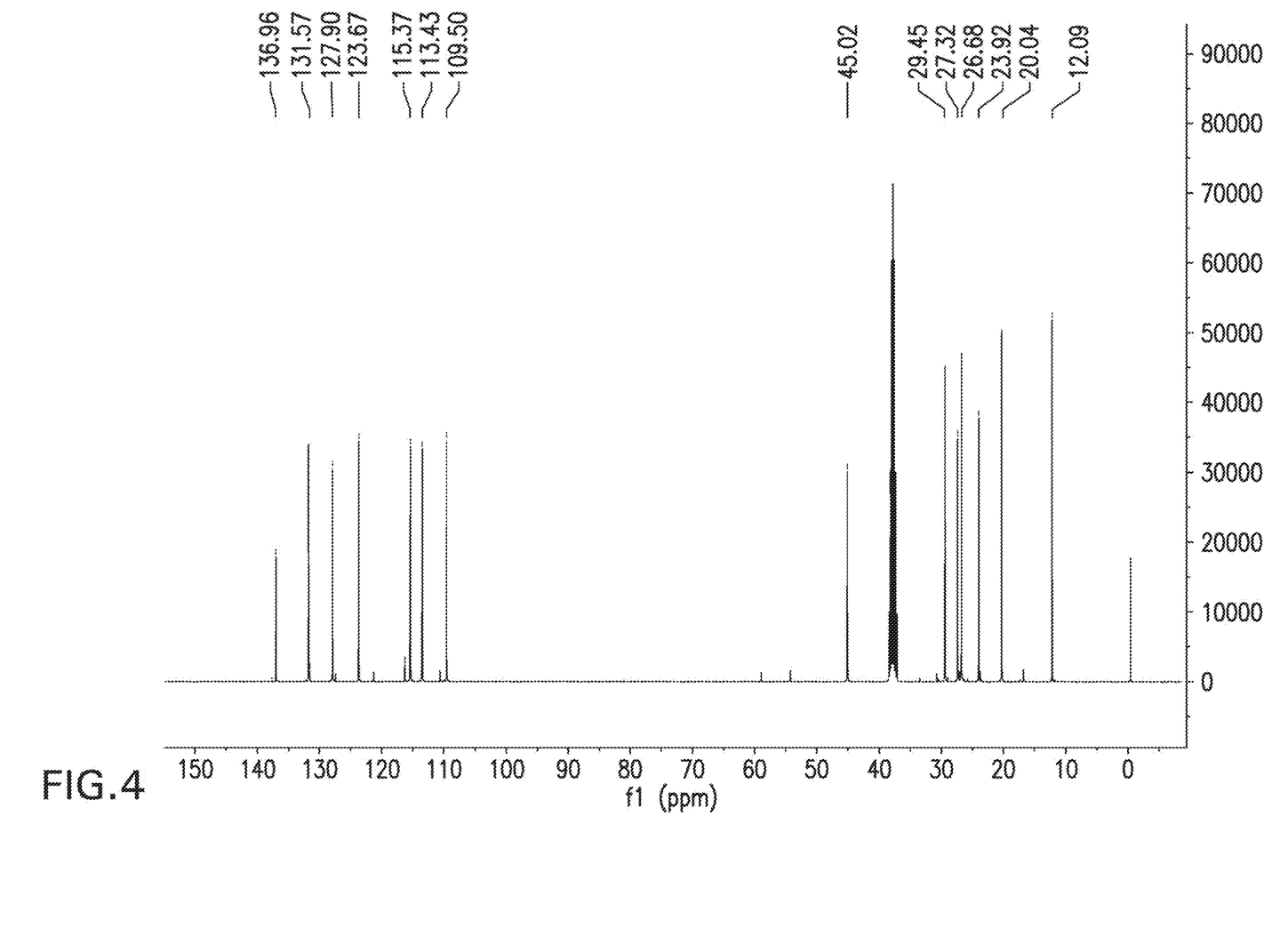

The $^1$H-NMR spectra also showed characteristic peaks corresponding to the respective structures of the ionic liquids. Characteristic peaks in the 9.10-7.52 ppm range confirmed the presence of an imidazolopyridine ring in the structure. Peaks for the aliphatic alkyl chain were also observed, such as the peak at or around 4.51 ppm was assigned to the CH$_2$ attached to the nitrogen of the imidazole ring. Similarly, other peaks were observed for the other aliphatic protons characteristic of their respective structures. A representative $^1$HNMR spectrum is shown in FIG. 3. The $^{13}$CNMR also showed characteristic peaks that represented the structures of the ionic liquids. A representative $^{13}$CNMR spectrum is shown in FIG. 4.

FIG. 3 and FIG. 4

Figure 5:
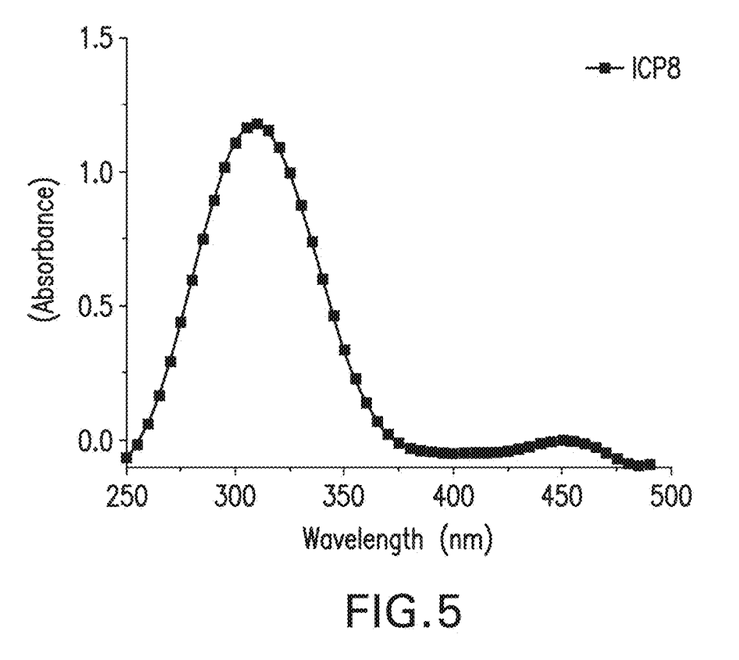

The UV-Vis absorption spectra of the ionic liquids in methanol were studied in the 200 nm to 800 nm wavelength range. All the derivatives showed absorbance at around 320 and 450 nm wavelengths. A representative UV-Visible spectrum is shown in FIG. 5.

FIG. 5

In Vitro Anti-*Candida* Activity

MIC and MFC of Ionic Liquids Alone

The anti-*Candida* activity of the ionic liquids and amphotericin B was articulated as MIC and MFC values against *C. auris* (Table 2). Progression of *C. auris* cells was not hindered in the presence of 1% DMSO, and the growth was similar to that of the positive control. Whereas the growth was severely impacted in the presence of all the ionic liquids. Among the tested ionic liquids, IPC8 displayed maximum antifungal efficacy with a MIC value of 4.88 µg/mL and MFC value of 9.76 µg/mL. Based on MIC and MFC results, the antifungal activity of newly synthesized ionic liquids follows IPC8>IPC6>IPC4≥IPC10>IPC12. The MIC and MFC values for amphotericin B against *C. auris* 2921 were 2 µg/mL and 4 µg/mL, respectively, which indicates that the tested *C. auris* strain was resistant to amphotericin B. The 3 to 8-fold lower MIC and MFC values of IPC8 as compared to other tested ionic liquids suggested promising antifungal activity of this compound against drug resistant *C. auris* isolates.

TABLE 2

Antifungal activities of ionic liquids and amphotericin B against *C. auris*.

| | Average MIC value (µg/mL) | Average MFC value (µg/mL) |
|---|---|---|
| IPC4 | 78.12 | 312.5 |
| IPC6 | 39.06 | 78.12 |
| IPC8 | 4.88 | 9.76 |
| IPC10 | 78.12 | 312.5 |
| IPC12 | 312.5 | 625 |
| Amphotericin B | 2.0 | 4.0 |

Time Kill Curves

Figure 6:
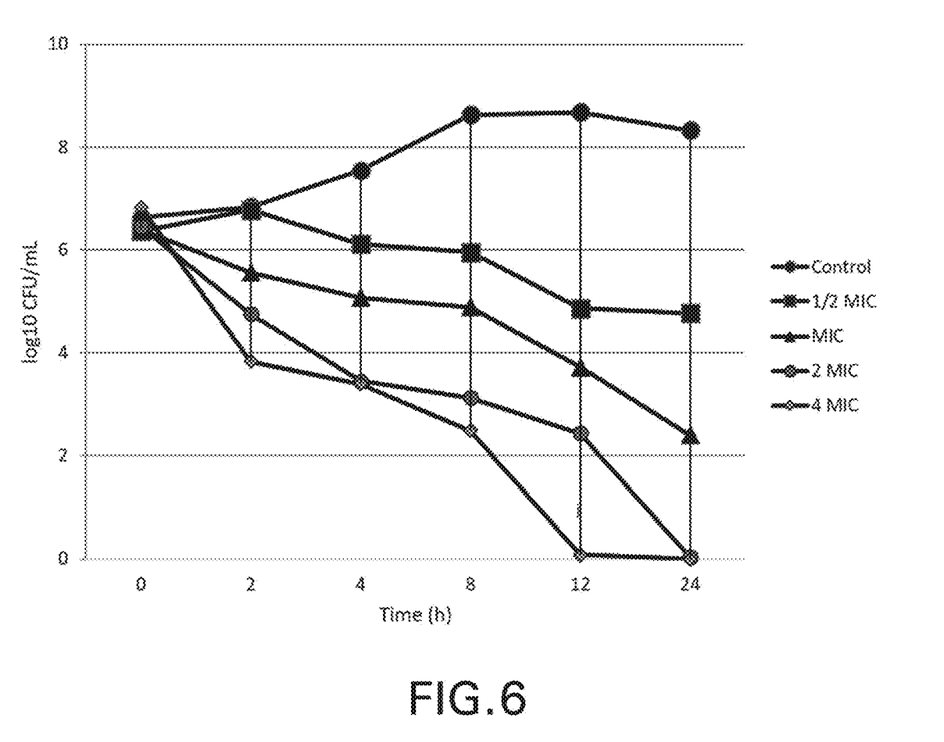

The results obtained revealed that IPC8 exerted fungicidal activity, which was concentration- and time-dependent (defined as a kill of ≥log 3) against the tested *C. auris* strain (FIG. 6). The median value of 2 times MIC was responsible for causing candidacidal endpoint after 12 h whereas, four times MIC resulted in candidacidal endpoint after 24 h. The average log 10 CFU/mL for healthy control was 7.78, which was reduced to 5.8 after 24 hr exposure to H MIC and 4.67 after 24 hr exposure to MIC. Furthermore, after treating with the MIC value of IPC8, a 50% reduction in the log 10 CFU/mL from the inoculum was observed after 12 h; however, with the increasing concentration, two and four times the MIC value, the 50% reduction in the number of CFU was achieved after 4 and 2 h respectively. The results obtained from the time-kill curve showed that IPC8 killed the *C. auris* strain at concentrations above the MIC value and further confirmed that the compound is fungicidal in nature.

FIG. 6

Antifungal Interactions of Ionic Liquids and Amphotericin B

To investigate the type of anti-*Candida* interactions of ionic liquids and amphotericin B, the checkerboard microdilution assay was performed. The checkerboard microdilution method, where the concentrations of the two compounds combined are studied, helped determine the total fractional inhibitory concentrations (ΣFIC), which in turn signifies the nature of the interaction between ionic liquids and amphotericin B. The data obtained showed synergistic (ΣFIC≤0.5), additive (ΣFIC>0.5-≤1), and no interaction interactions (ΣFIC>1-<2) of ionic liquids and amphotericin B for tested *C. auris* strain as shown in Table 3. Most importunately, the results showed that there was a four-fold decrease in the MIC of ionic liquid IPC8 as well as amphotericin B when used together. Therefore, the MIC value of IPC8 and amphotericin B was significantly reduced when used in combination; thus, combination therapy, while reducing the overuse of drugs, may give a suitable approach for combating resistance against commonly used antifungals.

TABLE 3

Combination values from the checkerboard microdilution assay.

| Compounds | Average MIC values of individual compounds (µg/mL) | MIC of ionic liquids in combination with AmB (µg/mL) | MIC of AmB in combination with ionic liquids (µg/mL) | FICa | FICb | ΣFIC | Type of interaction |
|---|---|---|---|---|---|---|---|
| IPC4 | 78.12 | 39.06 | 2.0 | 0.5 | 1.0 | 1.5 | No INT |
| IPC6 | 39.06 | 9.76 | 0.5 | 0.24 | 0.25 | 0.49 | SYN |
| IPC8 | 4.88 | 1.22 | 0.25 | 0.25 | 0.125 | 0.38 | SYN |
| IPC10 | 78.12 | 19.53 | 1.0 | 0.25 | 0.5 | 0.75 | ADD |

TABLE 3-continued

Combination values from the checkerboard microdilution assay.

| Compounds | Average MIC values of individual compounds (μg/mL) | MIC of ionic liquids in combination with AmB (μg/mL) | MIC of AmB in combination with ionic liquids (μg/mL) | FICa | FICb | ΣFIC | Type of interaction |
|---|---|---|---|---|---|---|---|
| IPC12 | 312.5 | 156.25 | 1.0 | 0.25 | 0.5 | 0.75 | ADD |
| AmB | 2.0 | — | — | — | — | — | — |

Figure 7:
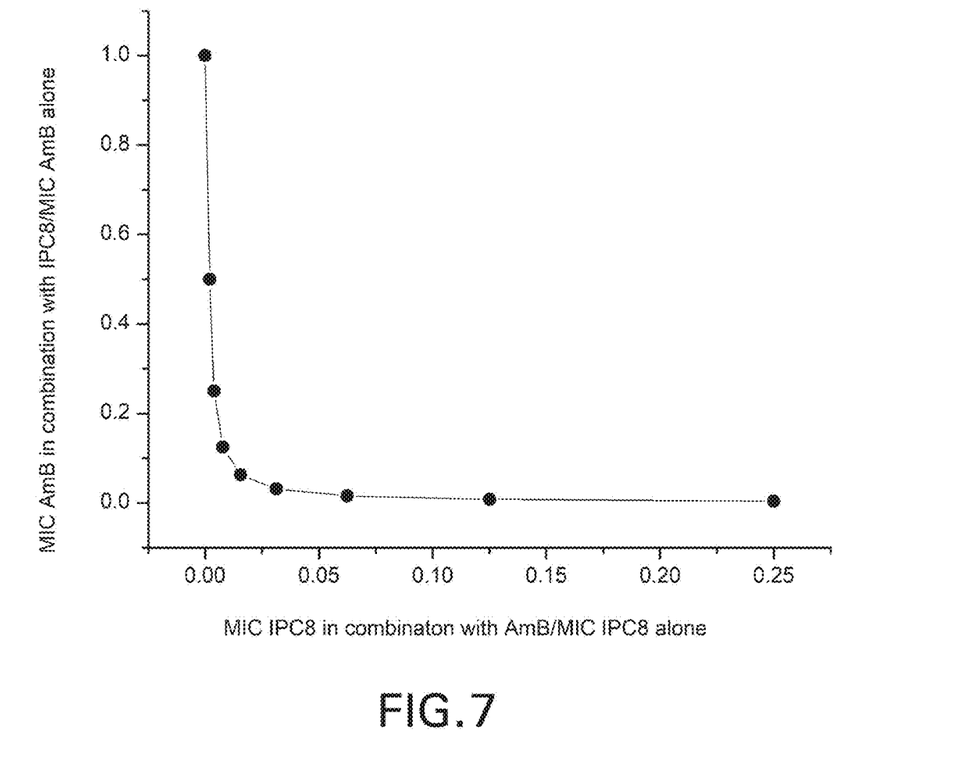

AmB = Amphotericin B; No INT = no interaction; ADD = Additive; SYN = Synergistic Combinatorial Effect of Ionic Liquids in Varied Ratios To evaluate the combined effect in various ratios, only the concentrations resulting in synergistic interactions were further used, and nine different ratios between ionic liquids and amphotericin B were prepared; the results are shown in the form of isobolograms (FIG. 7). Out of nine ratios of IPC8 and amphotericin B, seven displayed a strong synergistic effect against the *C. auris* strain, whereas the two interactions were additive in nature.

FIG. 7

Haemolytic Activity

Figure 8:
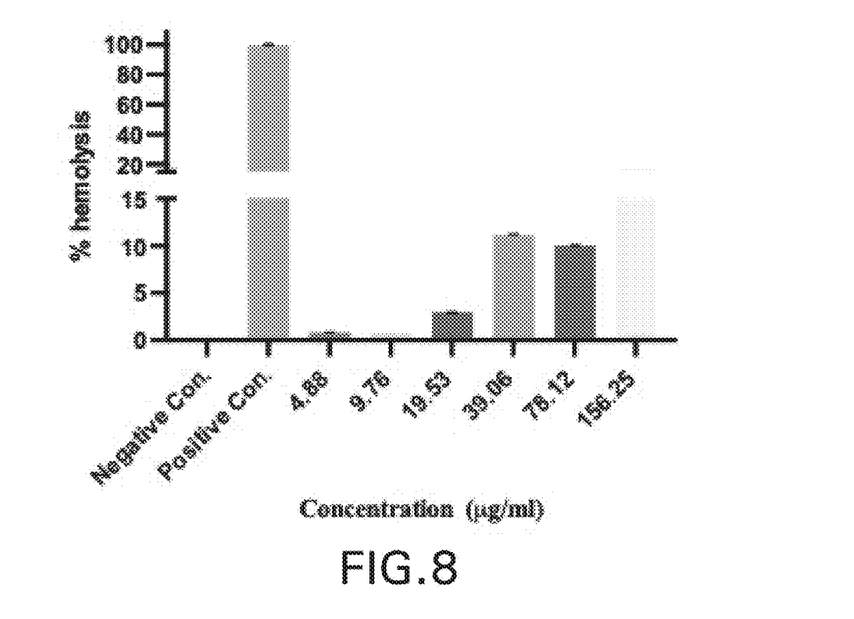

The commonly used drugs against *Candida* species possess a high risk of toxicity and, therefore, restrict their usage in critically ill patients. Henceforth, there is a pressing requirement to look for alternative options that result in targeted therapy without harming patients. Since IPC8 presented significant activity alone and in combination against *C. auris* cells, toxicity determination of IPC8 was highly imperative. IPC8 at various concentrations (4.88 μg/mL, 9.76 μg/mL, 19.53 μg/mL, 39.06 μg/mL, 78.12 μg/mL, and 156.25 μg/mL) was checked for its haemolytic activity. The samples treated with the triton X-100 showed clear haemolysis as there was the release of the cellular constituents into the solution. Whereas PBS treatment resulted in an intact cellular pellet giving an indication of a negative haemolytic result. The data obtained for IPC8 showed less haemolytic activity of IPC-treated RBCs; 16.14% haemolysis was observed at a concentration of 156.25 μg/mL (FIG. 8).

FIG. 8

While the invention has been described in terms of its several exemplary embodiments, those skilled in the art will recognize that the invention can be practiced with modification within the spirit and scope of the appended claims. Accordingly, the present invention should not be limited to the embodiments as described above but should further include all modifications and equivalents thereof within the spirit and scope of the description provided herein.

ACKNOWLEDGMENTS

This research work was funded by Institutional Fund Pro-jects under grant no. (IFPNC-003-135-2020). Therefore, the authors gratefully acknowledge technical and financial support from the Ministry of Education and King Abdulaziz University, DSR, Jeddah, Saudi Arabia.

What is claimed is:

1. A pharmaceutical composition having antifungal properties, comprising:
    at least one ionic liquid selected from the group consisting of 1-butylimidazo[1,2-a] pyridinium bromide (IPC4), 1-hexylimidazo[1,2-a] pyridinium bromide (IPC6), 1-octylimidazo[1,2-a] pyridinium bromide (IPC8), 1-decylimidazo[1,2-a] pyridinium bromide (IPC10), and 1-dodecylimidazo[1,2-a] pyridinium bromide (IPC12); and
    Amphotericin B.

2. A method of inhibiting growth of a fungus, comprising exposing the fungus to an effective amount of a composition comprising and Amphotericin B and at least one ionic liquid selected from the group consisting of 1-butylimidazo[1,2-a] pyridinium bromide (IPC4), 1-hexylimidazo[1,2-a] pyridinium bromide (IPC6), 1-octylimidazo[1,2-a] pyridinium bromide (IPC8), 1-decylimidazol[1,2-a] pyridinium bromide (IPC10), and 1-dodecylimidazo[1,2-a] pyridinium bromide (IPC12).

3. The method of claim 2, wherein the fungus is *Candida* spp.

4. The method of claim 2, wherein the fungus is *Candida auris*.

5. The method of claim 2, wherein the fungus is resistant to azole antifungal agents or Amphotericin B.

6. The pharmaceutical composition of claim 1 wherein the at least one ionic liquid is 1-octylimidazo[1,2-a] pyridinium bromide (IPC8).

7. The method of claim 2 wherein the at least one ionic liquid is 1-octylimidazo[1,2-a] pyridinium bromide (IPC8).

* * * * *